United States Patent [19]
Bull et al.

[11] Patent Number: 5,716,796
[45] Date of Patent: Feb. 10, 1998

[54] OPTICAL BLOOD HEMOSTATIC ANALYSIS APPARATUS AND METHOD

[75] Inventors: Brian S. Bull, Loma Linda; Ralph A. Korpman, Redlands, both of Calif.

[73] Assignee: Medical Devices Corporation, San Bernardino, Calif.

[21] Appl. No.: 593,483

[22] Filed: Jan. 29, 1996

Related U.S. Application Data

[60] Continuation of Ser. No. 193,738, Feb. 9, 1994, abandoned, which is a division of Ser. No. 896,539, Jun. 9, 1992, abandoned, which is a continuation-in-part of Ser. No. 468,594, Jan. 23, 1990, Pat. No. 5,184,188.

[51] Int. Cl.$^6$ .............................. C12Q 1/56; B05D 7/00
[52] U.S. Cl. .............................................. 435/13; 427/212
[58] Field of Search .................... 435/13, 969; 427/212, 427/219, 430.1; 436/69; 514/653

[56] References Cited

U.S. PATENT DOCUMENTS

| 3,944,687 | 3/1976 | Morisaki | 427/372 |
| 5,091,304 | 2/1992 | La Duca | 435/13 |

OTHER PUBLICATIONS

Wintrobe M., Clinical Hematology 7th Ed. 1974 Lea & Febiger, Phila.

*Primary Examiner*—Ralph Gitomer
*Attorney, Agent, or Firm*—Loeb & Loeb LLP

[57] ABSTRACT

A method for optically measuring the functional capacity of blood platelets and the blood clotting system. The method consists of detection of platelet aggregation in a platelet-containing specimen fluid, whereby the specimen fluid is contacted with a platelet agonist and disclosure reagent. A mechanical specimen-handling apparatus with one or more optical end-point detectors which is preferred for use with the method of the invention is also described. The apparatus incubates a small quantity of diluted whole blood with added solid or liquid reagents at body temperature, and mixes the blood via rocking and rotational motions so as to expose the blood uniformly to the reagents. The optical end-point detectors then measure the activity of platelets within the blood specimen, clotting time, and the clotting cascade. Several intermediate measurements are also available.

12 Claims, 4 Drawing Sheets

BACKWARD TILTED POSITION

FORWARD TILTED POSITION

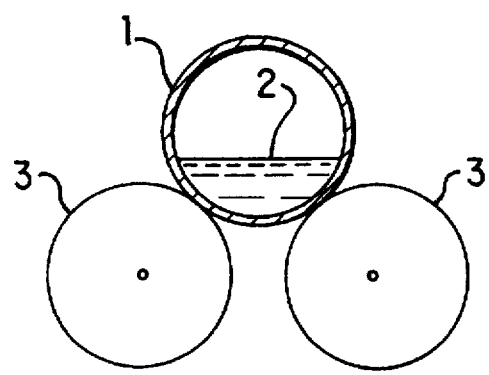
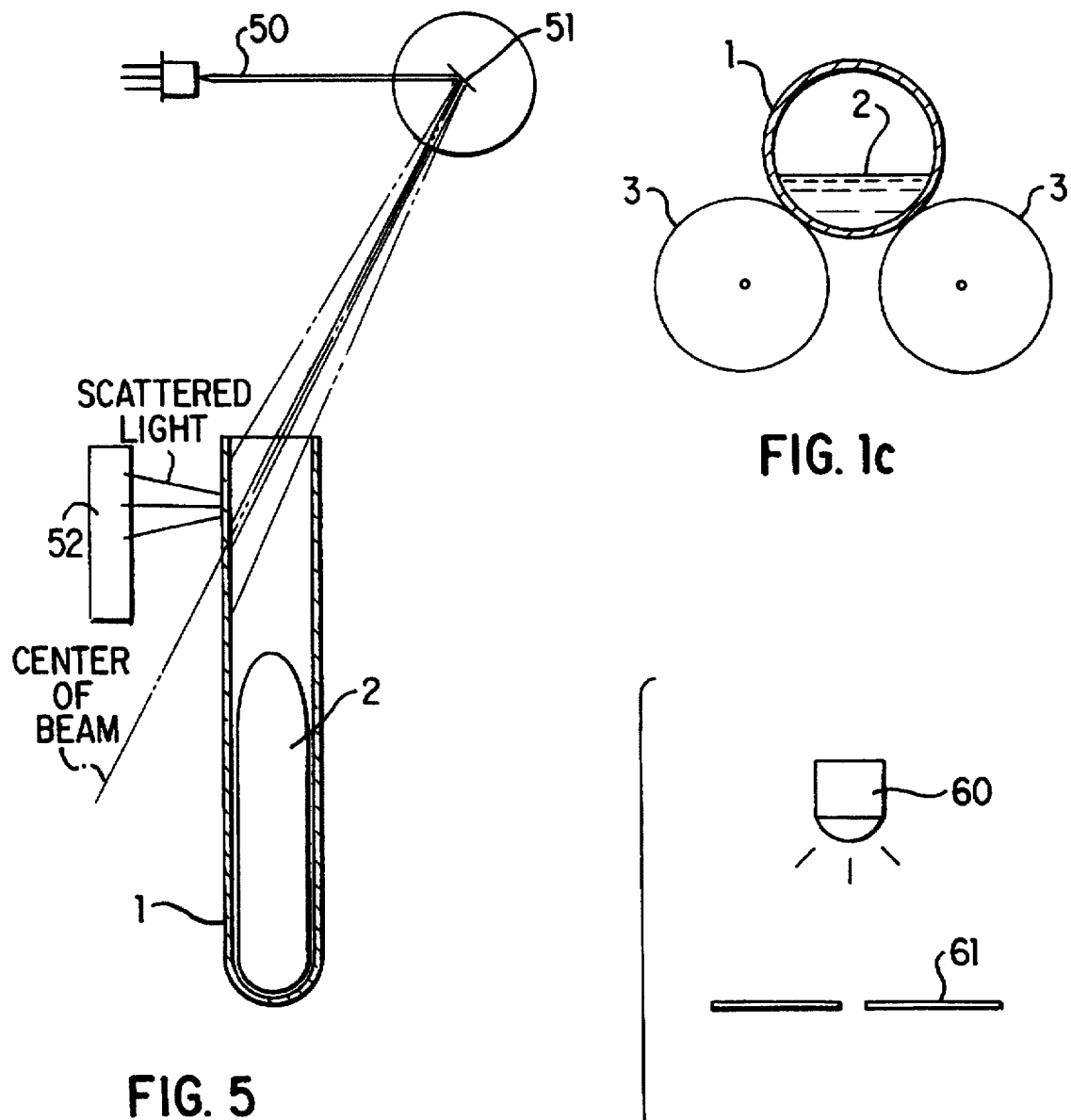
FIG. 5
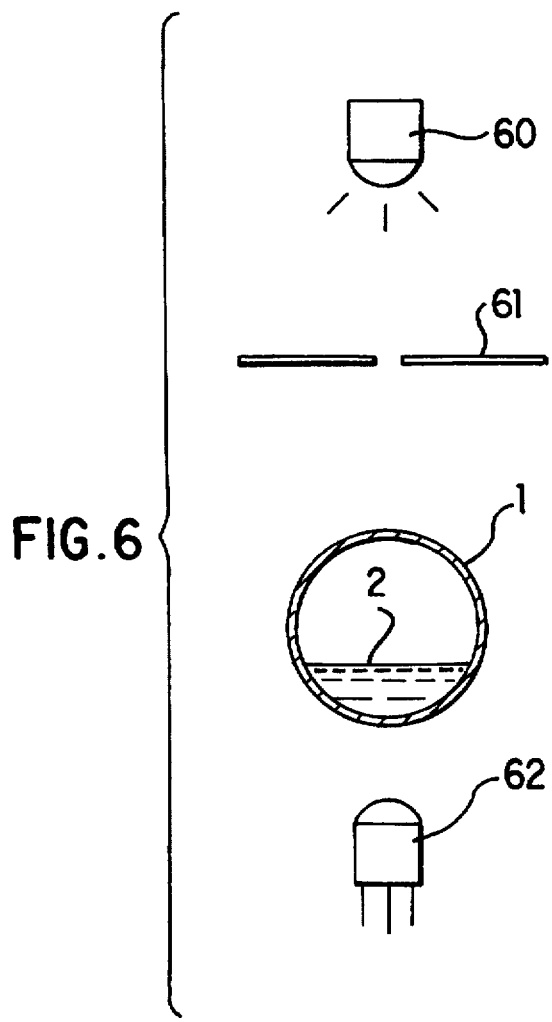
FIG. 1c
FIG. 6

OPTICAL BLOOD HEMOSTATIC ANALYSIS APPARATUS AND METHOD

RELATED APPLICATION

This is a continuation of application Ser. No. 08/193,738 filed on Feb. 9, 1994, now abandoned, which is a divisional application of Ser. No. 07/896,539, filed Jun. 9, 1992, now abandoned which in turn is a continuation-in-part application of Ser. No. 07/468,594, filed Jan. 23, 1990, now issued as U.S. Pat. No. 5,184,188.

BACKGROUND OF THE INVENTION

1. Field of the Invention

The invention relates to optical blood hemostatic analysis apparatus and methods, and more particularly to an apparatus and method for optically measuring the functional capacity of blood platelets and the blood clotting system.

2. Related Art

In the medical field, it is often desirable to measure and evaluate blood clotting times and blood platelet function, and more particularly, to determine the state of the platelets in circulation. For example, studies of platelet function and coagulation time are useful in the identification of patients who are at increased risk of thrombosis due to platelet hyperactivity or to blood hypercoagulability. They are also of use in the identification of patients who are at risk of bleeding due to platelet hypoactivity or to blood hypocoagulability. Devices for measuring these aspects of blood are therefore quite useful. The ability to determine the state of the platelets in circulation is important because it enables a relatively accurate assessment of the likelihood of forming a coronary thrombosis leading to myocardial infarction.

Separate blood clotting evaluation instruments and platelet function evaluation instruments have been known in the art. However, testing instruments for determining the state of the platelets in circulation are not available. A number of machines on the market for evaluation of blood clotting utilize a light beam for detecting the clotting end-point, but can only be used with plasma (a relatively clear fluid derived by removing the red cells). Very few blood clotting evaluation instruments can be used with both opaque whole blood and with plasma, but these are all believed to require physical contact with the specimen, and thus contain parts that are an infection hazard and must be carefully cleaned to avoid infectious propagation. In addition, such devices are difficult to clean reproducibly, potentially affecting test performance. This latter class of machine often uses a primarily mechanical end-point detector, and, for that reason, is prone to breakdown. One example of such an instrument is known as a fibrometer, which uses a metal probe.

Devices exist which are capable of evaluating platelet function, although the state of the platelets in circulation is not determined. It is believed that all of these machines operate with plasma and are single-purpose instruments. These machines are generally called platelet aggregometers. Aggregometers generally transmit a light through a suspension of platelet-rich plasma (plasma containing platelets) incubated at 37° C. (body temperature). Light shining through the suspension is generally refracted by the moving platelet surfaces. When aggregating substances are added, the platelets clump into large aggregates. This causes more light to get through to a photosensor on the far side of the measuring chamber, generating a detectable signal.

There is one aggregometer instrument available that purports to perform platelet function studies on whole blood (Chronolog Corporation, Haverstown, Pa.). It is believed that this device does not measure the formation of platelet aggregates, but rather the adherence of already formed platelet aggregates to a pair of metal wires. In addition, it cannot perform any clotting studies.

One reference is known that describes a device for optical indication of coagulation and concentration and aggregation of platelets, but can only be used with plasma (see U.S. Pat. No. 4,501,491). This reference also cites a number of other references in the field (see column 2).

It is therefore desirable to provide a single instrument that can analyze blood platelet function and clotting evaluation using whole blood. Such a machine should not require physical contact between the whole blood specimen and the analysis elements. It would also be desirable to provide an instrument capable of determining the functional state of platelets so rapidly after removal from the circulation that the results are similar to those that would have been obtained if the platelet functional state had been measured within the circulation. This requires that the test be done in whole blood with no preparatory modifications to the sample.

SUMMARY OF THE INVENTION

The inventive device is designed to measure the functional capacity of various distinct (but related) components of hemostasis: blood platelets and the blood clotting system. Furthermore, the device permits the native state of platelets in circulation to be determined. The preferred embodiment of the invention includes a mechanical specimen-handling apparatus with one or more optical end-point detectors. The apparatus incubates a small quantity of diluted whole blood at body temperature and mixes the blood via rocking and rotational motions so as to expose the blood uniformly to added solid or liquid reagents. It then measures at least two separate end-points. The first end-point is a measure of the activity of platelets within the blood specimen. The second end-point is a measure of the activity of the clotting cascade. Several intermediate measures are also available.

The purpose of the bimodal motion of the inventive apparatus is to maintain such a thin film of the specimen fluid over the entire inner surface of a specimen container. This increases the sensitivity of end-point detection by concentrating platelet clumps and fibrin polymer in the thin film.

Because the device is capable of measuring both blood platelet functioning and the blood clotting system, the performance of these tests renders the device capable of yielding information equivalent to a battery of the four separate screening tests presently in widespread use. These presently-utilized tests include platelet count, bleeding time, prothrombin time, and the activated partial thromboplastin time. Further, the device is capable of yielding this information on as little as 150 μl of whole blood.

At present, it is believed that all prior optical end-point detectors fail in the presence of red blood cells. The optical methods of end-point detection of the present invention are unique, in that they function effectively in the presence of red blood cells for the assessment of platelet function and in that they are enhanced by the presence of red cells in the detection of clotting end-point. As a result, the signal-to-noise ratio of the invention is effective for optical platelet function and substantially better than current blood clotting detectors.

The invention permits rapid estimation of platelet functional adequacy in a manner that is sensitive to the native state of platelets in circulation. Furthermore, decreases in both platelet number and platelet function may be assessed. The invention also permits evaluation of platelet functional activity in response to platelet aggregating and platelet stimulating agents (e.g., arachidonic acid, adenosine diphosphate, ristocetin, epinephrine, collagen, etc.), and study of the effects of antiplatelet agents used clinically for modulation of platelet function (e.g., aspirin, sulfinpyrazone, dipyridamole, etc.). The invention can also be used to evaluate the effects of anticoagulants on the blood coagulation reaction (e.g., when monitoring the clinical use of heparin, coumadin, and related anticoagulants).

Diatomaceous earth may be used as a disclosing reagent to assess platelet activity and/or the blood clotting mechanism. In addition to diatomaceous earth, a diluent may also be employed. The order in which the whole blood, diatomaceous earth, and/or the diluent are combined permit the measurement of a variety of test parameters. For instance, tests may be performed to screen for defects in the entire blood coagulation pathway, to permit the assay of platelet function and number, and/or to indicate the likelihood of the formation of a coronary thrombosis.

The preferred embodiment of the inventive device can simultaneously screen both blood platelet function and coagulation in opaque whole blood. If desired, the inventive device can provide, on additional test runs, specific information on platelet response to platelet stimulating agents.

Significant advantages of the inventive apparatus and method include the following:

1. The invention utilizes a minute sample of blood (approximately 150 μl).
2. The invention operates with whole blood, obviating many sample preparation problems.
3. The invention measures simultaneously the platelet and clotting components of the hemostatic mechanism (except for factor XIII activity).
4. The invention requires no physical contact between the analysis elements and the blood specimen.
5. The invention provides the first simple, fully automated routine test for platelet function. This is beneficial for such uses as assessing cardiovascular therapy regimens which depress platelet function (such as aspirin treatment).
6. The invention is capable of measuring platelet functioning so rapidly after specimen acquisition so as to determine the native state of platelets in circulation. It is thus sensitive to the presence of highly labile substances present in the circulation such as nitric oxide and prostacycline which modulate platelet function and have short half-lives.

Further aspects of the present invention will become apparent from the following detailed description when considered in conjunction with the accompanying drawings. It should be understood, however, that the detailed description and the specific examples, while representing preferred embodiments of the invention, are given by way of illustration only.

BRIEF DESCRIPTION OF THE DRAWINGS

FIG. 1c is a diagrammatic end view of the apparatus shown in FIG. 1a.

FIG. 3b is a diagrammatic end view of the apparatus shown in FIG. 3a.

FIG. 5 is a diagrammatic side view of one embodiment of an automatic sticking time and clotting time end-point detector for use in conjunction with the present invention.

FIG. 6 is a diagrammatic end view of one embodiment of an automatic clumping time end-point detector for use in conjunction with the present invention.

Like reference characters in the various drawings refer to like elements.

DETAILED DESCRIPTION OF THE PREFERRED EMBODIMENT

Overview

Two fundamental problems that had to be overcome by the present invention in order to combine platelet function testing and coagulation testing were timing and end-point detection. Timing is a problem because thrombin, necessary to the clotting mechanism, is one of the most potent stimulators of platelet aggregation known. Thus, if clotting occurs before platelet aggregation is complete, then the thrombin generated in the course of clotting will rapidly aggregate the platelets. End-point detection is a problem because the detectors must be able to discriminate between platelet aggregation and clot formation, and ideally must do so in whole blood to avoid the artifacts induced by the process of preparing platelet-rich plasma. Although some mechanical detectors (such as the fibrometer) and some magnetic detectors (such as certain automated activated coagulation timers, or "ACT's") will work with whole blood, both introduce foreign objects into the blood: in the case of the fibrometer, a metal probe, and in the case of automated ACT devices, a cylindrical magnet. Further, neither of these devices can detect platelet aggregation in advance of blood clotting.

The timing problem was solved in the present invention by diluting the blood sample to delay the onset of clotting, and then making the platelet aggregation visible to measurement (even in the heavily diluted sample) using an activating matrix such as diatomaceous earth coated with an organic activator. The diatomaceous earth both activates the platelets and provides a matrix for platelet clumping which is large enough to disclose easily that aggregation is taking place. All of this activation and aggregation recognition transpires before any thrombin is generated from the clotting cascade. At the high specimen dilution utilized in the inventive system, a thin layer of whole blood drawn up onto the inner wall of a specimen container is sufficiently transparent to permit optical end-point detection. This has the considerable advantage of not introducing foreign measurement objects into the specimen fluid. It also eliminates the need to wash probes and replace the single use magnets used in some prior art detection devices.

The Mechanical Apparatus

The mechanical aspect of the invention includes an apparatus capable of both rotating and rocking a transparent, approximately cylindrical specimen container (for example, a 12×75 mm glass test tube) while maintaining the container in a nearly horizontal position and at a temperature of approximately 37° C. Whole blood, diluent, and a variety of platelet agonists are introduced into the open end of the container and are then mixed and incubated by the apparatus.

Figure 1A:
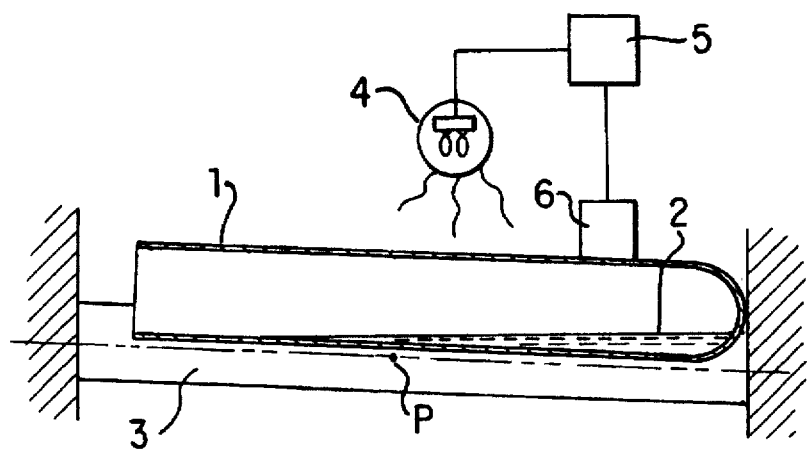
FIGS. 1a and 1b are diagrammatic side views of the preferred embodiment of the invention, showing the two positions in the rocking motion of the apparatus.
Figure 1B:
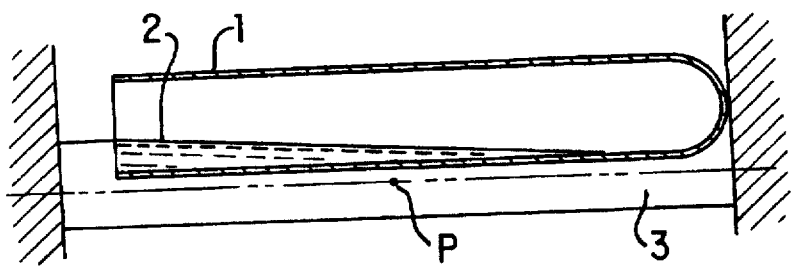

One embodiment of the mechanical apparatus of the invention is illustrated in FIGS. 1a and 1b, which shows a specimen container 1 containing specimen fluid 2 and which is supported in a nearly horizontal position on a pair of rotating rollers 3. FIG. 1c is an end-view of the apparatus shown in FIGS. 1a and 1b. The rollers 3 may be rotated by any convenient means, such as an electrical motor coupled to the rollers either directly or through a drive train (e.g., a belt, gears, or a friction drive). In the preferred embodiment, the specimen container 1 is rocked longitudinally around an approximate mid-point pivot P through an angle of preferably about ±3°, as shown by comparing FIG. 1a with FIG. 1b. The rotational rate of the specimen container 1 is typically about 12 rpm, and the rocking rate is typically about 15 cycles per minute. The rocking motion may be imparted by a cam or any other convenient means. The specific rocking and rotation rates are not necessarily critical, but the particular values described above have been found to be effective.

The specimen fluid 2 does not run out of the open end of a small-diameter specimen container 1 when tilted forward because of the strong surface tension of the contained fluid, aided by the small radius of curvature of the rim of the container 1. This means that the entire length of the bottom of the container can be coated with the specimen fluid during a rocking cycle. Because of the rotation of the specimen container, the entire inner surface of the specimen container 1 is coated with a thin layer of specimen fluid as the container wall rotates through the pool of specimen fluid 2 moving back and forth in the bottom of the container 1.

The purpose of the bimodal motion of the inventive apparatus is to maintain just such a fairly uniform thin film of the specimen fluid over the entire inner surface of the specimen container. This increases the sensitivity of end-point detection by concentrating platelet clumps and fibrin polymer in the thin film. Any comparable means of accomplishing this goal is within the scope of this invention, including simple rotation or agitation of a sealed container, or use of a container having a liquid retention rim at its opening.

Since the process works best at 37° C., it is desirable to maintain the specimen at that temperature. The temperature of the specimen fluid can be maintained, for example, by a tungsten filament light bulb 4 situated near the specimen container 1 and controlled by a thermostatic circuit 5 having a temperature sensor 6 adjacent to or in contact with the specimen container 1.

Alternatively, the temperatures can be maintained by placing the specimen container 1 in an incubated chamber having the desired temperature.

Specimen Fluid Preparation

A disclosure reagent, with or without modification of its surface by added organic activating compounds (e.g., humic acid, amino acid polymers, etc.), is used to initiate and also to disclose platelet aggregation. The disclosure reagent should have a high index of axial rotation which presents a maximum surface area and type of surface for platelet aggregation. Suitable disclosure reagents include diatomaceous earth, finely chopped glass, or finely chopped fiberglass. Those of skill in the art will know of other suitable disclosure reagents or can readily discern such without undue experimentation.

Many substances could be employed for the disclosure reagent. All that is required of the substance is a high axial ratio (long and skinny) and a small size relative to platelets so that the platelets can bind individual particles together into an easily-visible clump. Diatomaceous earth possesses all of the aforementioned characteristics. It is also cheap and readily-available. As a positive rather than a negative, this earth is coated with a polymer of amino acids (organic molecules often referred to as humic acid) that posses some of the characteristics of collagen. This is important because collagen is a molecule that platelets recognize and which activates them. Unfortunately, the natural concentration of this molecule in native diatomaceous earth, such as the earth extracted from the mines near Lompoc, Calif., is high enough to adequately stimulate only about two-thirds of normal platelets. The epinephrine coating raises this figure to a stimulation rate of over 99% of normal platelets.

Materials such as nylon fibers and the like could be used for the disclosure reagents, but these fibers would need to be coated with polymers of the appropriate amino acids and/or epinephrine to be as effective as epinephrine-potentiated Celite™ (Johns Manville's trade name for diatomaceous earth from the Lompoc mines). Celite™ that has been calcined (heated to a cherry red color) lacks the organic component and thus behaves as nylon fibers would.

Even though the calcium carbonate content of diatomaceous earth might vary from lot to lot, this does not pose a problem. The calcium carbonate content of the diatomaceous earth is not critical because more than enough calcium is added to the diluent to reverse any citrate present in anticoagulated blood.

The invention preferably utilizes a platelet agonist substance of some sort to activate the disclosure reagent, i.e., the diatomaceous earth. Naturally occurring diatomaceous earth is frequently coated with a weak platelet agonist substance. Other types of agonists such as arachidonic acid, ristocetin, and ADP can be added to the calcined material. Without an agonist, the calcined material will cause clumping and sticking in only a very small minority of patients; even then the times involved are well outside the normal ranges for the uncalcined epinephrine-potentiated material. Other related compounds, such as dopamine or noradrenaline, would function as well as epinephrine does in the capacity of a platelet agonist. All that is really required of the agonist substance is a general heightening of platelet sensitivity to the more usual agonists (thrombin, collagen, and epinephrine). Epinephrine accomplishes this function physiologically; hence, it may be utilizes in the present invention. The mix of amino acids is only for the purpose of simulating collagen; there is suggestive evidence that this is due to repeating lysine residues. Collagen is a most useful agonist simply because exposed collagen fibers are the normal inciting agent which brings about the start of platelet activation in the body.

The disclosure reagent can be used to activate the platelets, disclose that aggregation has occurred, or it may serve both functions. It also provides a matrix for platelet clumping which results in clumps large enough to disclose easily that aggregation is taking place. The rocking movement imparted by the inventive apparatus is necessary to keep the disclosure reagent particles in suspension so that they are constantly accessible to the platelets. The platelets reveal their activity by the rate at which they adhere to the disclosure reagent particles, and thus agglutinate into visible clumps. These clumps finally become sticky and adhere to the specimen container wall. Rotation of the container carries the platelet clumps out of the specimen fluid to the upper portion of the container where they can be detected without the interfering effect of the pool of specimen fluid in the specimen container.

Preparation of a specimen preferably comprises placing a small sample of whole anticoagulated blood (typically 150 µl) suspended in saline (typically 450 µl) in a specimen container to which has been added a small quantity of activated disclosure reagent (e.g., diatomaceous earth coated with an organic substance functioning as a platelet agonist such as humic acid or epinephrine), together with sufficient calcium ion to recalcify the blood sample. These reagents have been found to be stable and require no refrigeration, while permitting determination of platelet function and blood coagulation simultaneously.

The time from the moment the blood is added to the calcium-rich saline suspension to the moment the platelet clumps become visible in the specimen fluid is called the "clumping time". The time from the moment the blood is added to the saline suspension to the time when the platelet clumps stick to the wall of the specimen container is called the "sticking time". These two times are clinically significant and it is an object of the invention to measure both times.

A third effect which occurs in such blood samples at a later time is that the fibrinogen in the recalcified suspension begins to polymerize and entrap red blood cells. When this happens, the inner surface of the specimen container becomes coated with a thin opalescent layer which can be recognized as the onset of clotting, well before gross clots finally appear. The time from the addition of the blood to the specimen container to the time of formation of the fibrin net is called the "clotting time".

Comprehensive Hemostatic Mechanism Testing

In a number of surgical procedures, such as cardiac bypass or liver transplantation, it is important to know the platelet function status and the coagulation status of the patient. With such knowledge, medical personnel may select the appropriate blood component for control of post-operative bleeding. At present, a screen of the hemostatic mechanism requires ordering typically three tests, and takes typically 30 minutes. The minimum number of tests are platelet count, a platelet function assessment, and a test of clotting such as the automated partial thromboplastin time.

When diatomaceous earth is used as the disclosing reagent, it has been found that by mixing fresh whole blood with dry diatomaceous earth and then adding diluent to the mixture, a small amount of red cell lysis occurs. This releases adenosine diphosphate (ADP), a substance which acts as a platelet aggregation agonist. ADP causes accelerated platelet clumping onto the diatomaceous earth particles, and causes the platelet clumps to stick to the walls of the specimen container within typically 50 to 60 seconds. The appearance of platelet clumps adhering to the walls of the specimen container within this time frame indicates both that the platelet number is adequate and that the platelets present are capable of a normal response to the physiologic agonist ADP. Since no anticoagulant is present in this mixture, clotting will occur between about 100 to about 130 seconds if the coagulation pathway is normal. Thus, within less than three minutes using only 150 µl of whole blood, a comprehensive screen of the entire hemostatic mechanism (platelet number, platelet function, and coagulation) is accomplished by the present invention. This is a significant improvement over the 30 minute period of the prior art which requires multiple instruments and a larger quantity of blood to obtain these measurements.

Alternatively, if the diluent is added first to the diatomaceous earth, and the fresh whole blood contacts only wet diatomaceous earth, then platelets do not clump or stick immediately because no ADP is released and platelet aggregation is inhibited in blood for some 10 to 40 minutes after withdrawal from circulation. Under these circumstances, only Factor XII activation occurs, setting off the coagulation cascade. If, however, the blood has been withdrawn from the circulation about 10–40 minutes previously, and the disclosure reagent presents to the platelet critical amino acid sequences such as characterize collagen or basement membrane, then the resultant clumping reflects platelet response to such agonists. A third option, diluting the fresh whole blood before it contacts dry diatomaceous earth, produces an intermediate effect as compared to the two alternatives described immediately above.

The diatomaceous earth material can be activated by being treated with a catecholamine, such as adrenaline (epinephrine), noradrenaline, dopamine or others. Preferably, the catecholamine of this invention is epinephrine, because epinephrine is inexpensive and readily-available. A small amount of epinephrine (adrenaline) and saline is added to the diatomaceous earth, followed by lyophilization. The final concentration of epinephrine is approximately 0.5 millimoles. This dried reagent, lyophilized, epinephrine-enhanced, diatomaceous earth (LEEDE), is stable at room temperature for an indefinite period of time. Epinephrine acts as a platelet stimulant such that after exposure to the epinephrine-coated diatomaceous earth, platelets uniformly and avidly aggregate. The sequence of exposure of the LEEDE allows an analysis of different aspects of the hemostatic mechanism. The LEEDE is available from underground deposits, and, for example, may be mined from the deposit near Lompoc, Calif.

The lyophilization process does not freeze dry blood and diatomaceous earth; it only freeze dries epinephrine and diatomaceous earth. The purpose is primarily to aid in dispensing the correct amount of the reagents (it is easier to measure volume repeatedly than to determine weight repeatedly in the milligram range), and to prolong the shelf-life of the dispensed reagent. Other transformations may or may not occur during the freeze drying process; however, the activity of the mixture is generally preserved when the mixture is rehydrated. In the event that some activity is lost during the lyophilization process, this can be easily remedied by increasing the amount of epinephrine added before the freeze drying step.

When dried LEEDE is added to blood that has been drawn twenty minutes to two hours earlier, the coagulation system is strongly activated and the sample clots in about 120 seconds. This test is useful as a screen for defects in the entire pathway for blood coagulation.

When the LEEDE is dissolved in saline before being added to blood (drawn twenty minutes to two hours earlier), the coagulation system contact factor complex is less well activated, and the primary effect is seen on the platelets. The platelets clump to each other and to the diatomaceous earth particles and thereafter to the walls of the glass container. Therefore, the addition of dissolved LEEDE to the blood allows assay of both platelet function and number, before the blood clots.

If the LEEDE is dissolved in saline and then immediately added to blood which has just been drawn from the circulation, the length of time before the platelets clump appears to be a measure of the state of inhibition which characterizes native platelets in the circulation. The inhibition is due to circulating substances such as prostacyclin and nitric oxide and possibly other similar biologic effectors released from normal intravascular endothelium. These substances have short half lives of a few minutes, and thus have virtually disappeared by approximately 20 minutes after venipuncture. The ability to determine the state of the platelets in the circulation, as demonstrated above, is of great importance in medical practice. For example, this test could indicate the likelihood of forming a coronary thrombosis leading to myocardial infarction. A test of this nature is currently unavailable.

Raw data for the method and apparatus of the present invention (the HEMECH screen) have been acquired. The normal ranges of times for the HEMECH screen are: (1) Epinephrine Clumping Time: 28.7–43.1 seconds; (2) Epinephrine Sticking Time: 36.6–54.5 seconds; (3) Epinephrine Clotting Time: 142.6–165.1 seconds.

End-point Detection in General

Detection of the clumping, sticking, and clotting times can be by a variety of means that detect the respective end-points. A number of different types of end-point detectors can be used in the invention. One is direct visual observation. A second is a flying spot scanner, arranged such that a spot of light (visible or infrared) is aimed to normally miss a photosensor array fixed inside the transparent specimen container parallel to its axis of rotation. Sticking platelet clumps cause refraction of the light spot such that the light momentarily falls on the photosensor, generating a transient signal. Clots become distributed in a thin layer on the inner surface of the transparent container and refract light approximately constantly. The photosensor registers the presence of clots as increased, relatively steady illumination. A variation of this type of detector uses steady illumination and electronically scans an array of photosensors mounted along the axis of the specimen container.

A third end-point detector consists of a narrow beam of light (e.g., from a small, solid state laser) that is caused to sweep (e.g., by means of an oscillating mirror) the inner wall of the transparent specimen container from a position just outside the open end of the container. As with the flying spot scanner, the beam traverses the container wall and is aimed to miss an externally-placed photosensor. As platelet clumps stick on the wall of the container, they refract the light sufficiently so that a portion of the light beam strikes the detector in a time-varying amount, corresponding to the passage of each clump. Clotting produces a steady increase in the light striking the photosensor.

A fourth device detects only platelet clumping. It uses a light beam and a time-delay discriminator circuit which distinguishes the presence of platelet clumps from the rocking surface of the blood itself. As clumps pass the optical detector, they create detection events shorter than the delay time, and are distinguishable from the smooth "sloshing" of the specimen fluid in the rocking container. This type of detector may be combined with the second or third type of detectors described above for a fully automated optical analysis instrument that indicates clumping, sticking, and clotting times.

The principle used in the inventive apparatus to detect coagulation has substantial merit apart from detection of platelet function. Because of the rotating and rocking motion of a specimen container, platelet clumps stick to essentially the entire inner surface of the specimen container wall before fibrin polymerization begins. A useful coincidence is that platelets also form the physiologic nidus for fibrin polymerization. Thus, as the earliest fibrin polymers form (the beginning of a clot) they are caught by the platelet clumps rotating through the pool of specimen fluid and sieve the diluted reaction mixture. Essentially, all the polymerized fibrin in the specimen fluid is caught and "appliqued" to the wall of the specimen container. In this position, the polymerized fibrin traps red cells which block any light beam that traverses the specimen container wall. This causes generation of a very large signal when clotting occurs. In comparison, other optical end-point detectors in common use pick up a very modest change in opacity as fibrin polymerizes throughout a transparent bulk reaction mixture. The present invention thus achieves an enormous biological amplification of signal in comparison to background noise by mechanical concentration of the fibrin on the wall of the specimen container, where the fibrin can easily be seen by an optical end-point detector.

Illustrated Embodiments

Figure 2:
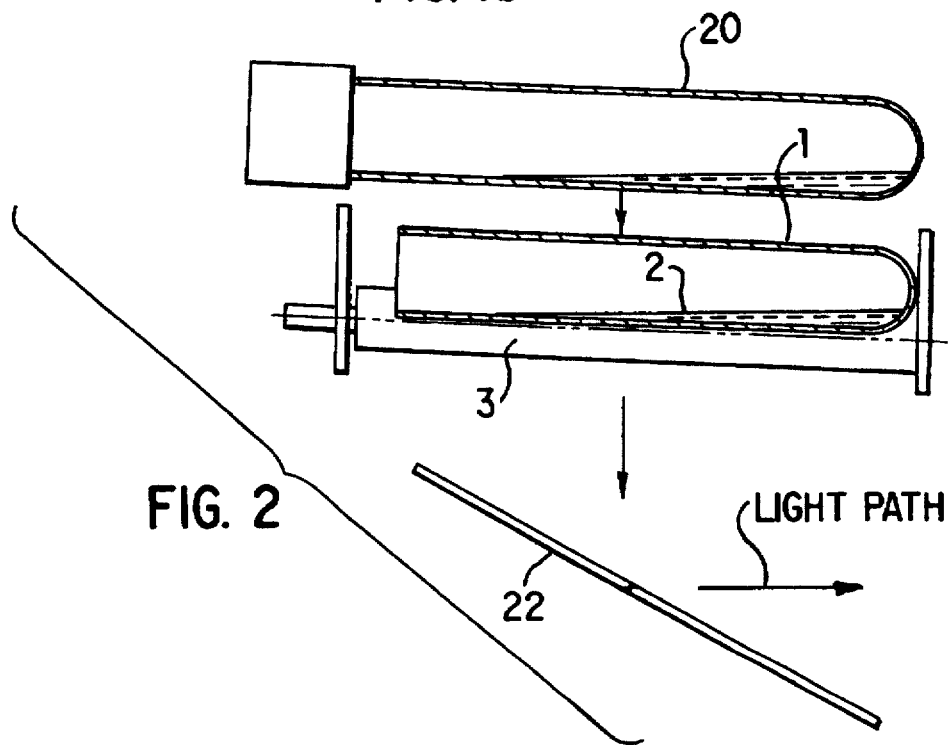
FIG. 2 is a diagrammatic side view of one embodiment of a setup for detecting clumping time, sticking time, and clotting time by visual observation.

One means of detecting the desired end-points in a properly prepared specimen using the present invention is by manual observation. FIG. 2 shows a diagrammatic view of one setup for such observation. A baffled light source 20 is situated such that light passes from above the specimen container 1 only through the container 1. An angled mirror 22 may be placed beneath the specimen container 1 for ease of observing the bottom of the container 1. Preferably, the baffled light source 20 is placed such that the light passing through the specimen container 1 is reflected by the mirror 22 to the eye of an observer without glare. When a specimen container 1 is viewed from below, any particles collecting along the lower surface of the specimen container 1 or any change in the content of the container 1 can be seen. The clumping, sticking, and clotting times can thus be manually timed.

In general, it is preferable to detect the desired time end-points automatically. However, such detection is complicated by the fact that the containers are rocking as well as rotating. Further, since the specimen fluid moves back and forth along the length of the specimen container, platelet clumps may stick anywhere along the container. Therefore, once platelets stick to the wall of the container, the detector must indicate their presence wherever they may be. Before the clumps stick, they do move in the fluid along the length of the container. While a fixed detector somewhere along the container can be used for just this situation, a more comprehensive detection system is preferred.

It has also been found that measurement results from automatic detection apparatus are at times inaccurate due to imperfections in the optical qualities of the specimen containers, and because red blood cells and disclosure reagent (e.g., diatomaceous earth) can cling to the interior wall of a specimen container. Although a human observer can easily detect and compensate for such sources of error, it is much more difficult to provide an automatic detection system that can compensate as well. It has therefore been found preferable in most instances to use a light source and photosensor system situated such that the light beam passes through the wall of the specimen container only once, thereby halving such problems. This limitation can be eased or removed if specimen containers having high optical quality are used, and/or if the background signal "noise" caused by blood cells and disclosure reagent clinging to the interior wall can be reduced to a satisfactory level.

Figure 3A:
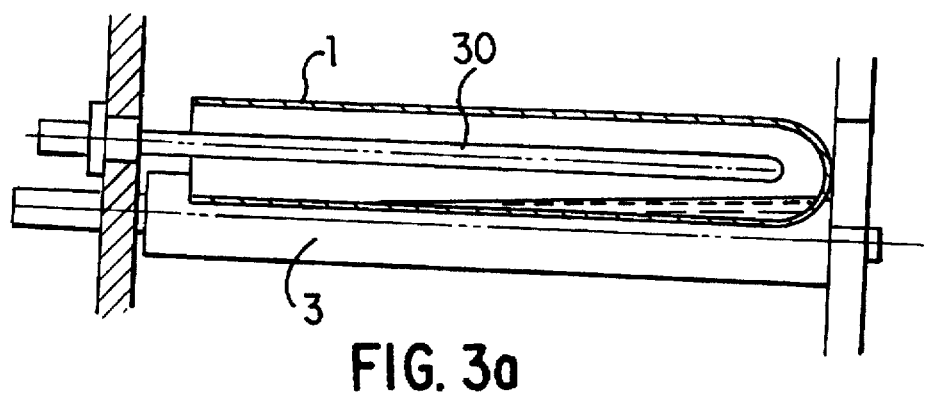
FIG. 3a is a diagrammatic side view of one embodiment of an automatic sticking time and clotting time end-point detector for use in conjunction with the present invention.
Figure 3B:
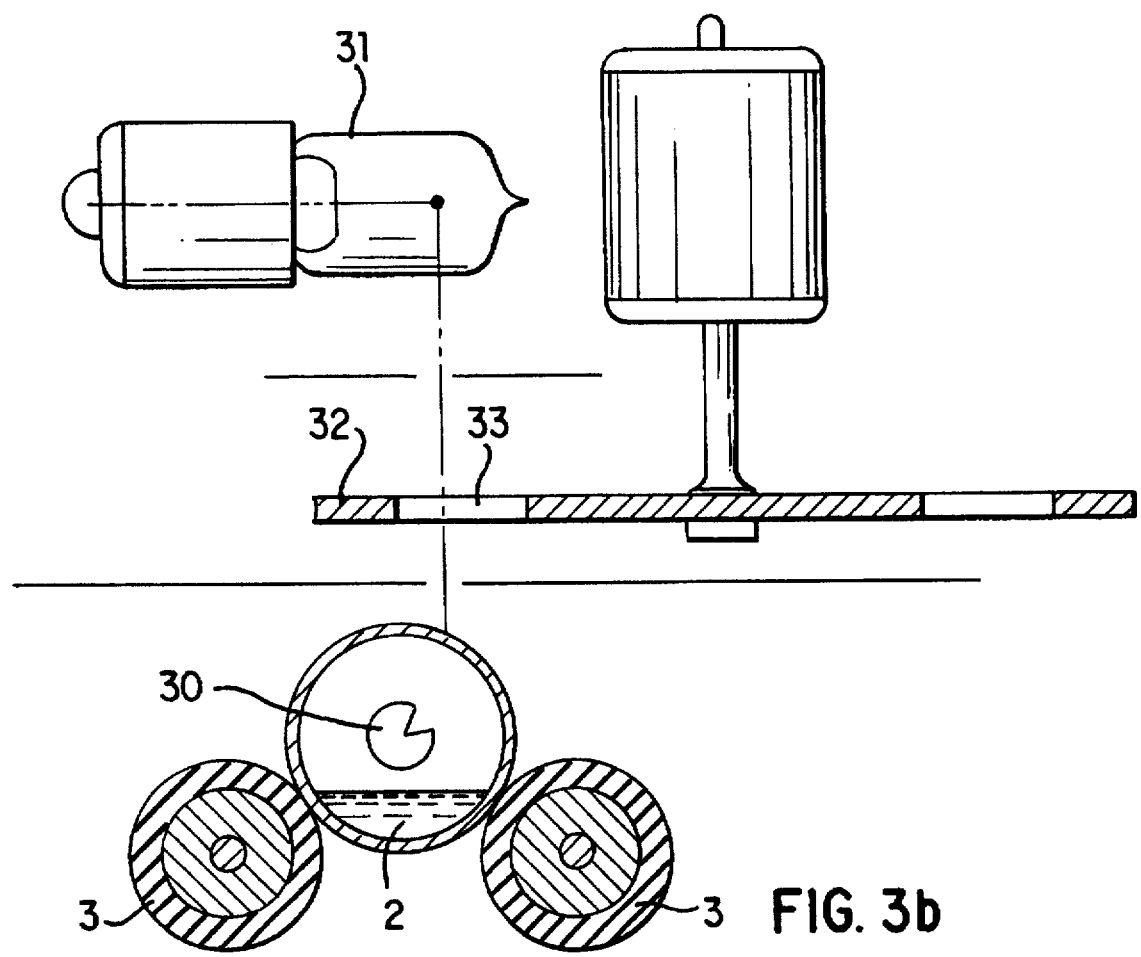

One automatic detection apparatus that detects the sticking time and clotting time for a specimen fluid is shown in FIGS. 3a and 3b. The detector element comprises an array of photosensors (e.g., photodiodes or phototransistors) 30 placed in a transparent container approximately the length of the specimen container 1, and of a diameter substantially less than the inner diameter of the specimen container 1. The sensor array 30 can thus be inserted into the specimen container 1 along the axis of the container 1, thus avoiding contact with the specimen fluid 2. The sensor array 30 is affixed to the roller and rocking mechanism such that it rocks back and forth with the specimen container 1. A linear lens or a light baffle on the sensor array 30 is preferably used to limit the acceptance angle of light to the sensor array 30 to about ±10°. A light source 31 is provided adjacent the specimen container 1 and baffled such that a thin line of light passes through the specimen container 1, but to one side of the opening of the sensor array 30. This arrangement illuminates the entire length of the specimen container 1. Wherever a platelet clump sticks to the wall of the container 1 such that it rotates around as the container 1 rotates and therefore intersects the line of light, the clump scatters the light so that some of it enters the unbaffled opening of the sensor array 30.

Because the interior of the container is constantly coated with specimen fluid as it rotates, the signal to noise ratio of platelet clumps to specimen fluid coated on the interior wall is not as great as might be desired. To improve the signal to noise ratio, a rotating shutter 32 incorporating a number of radial slits 33 can be positioned as shown in FIG. 3 so that the radial slits 33 intersect the line source of light. This, in effect, restricts the line source of light to "flying spots" of light which scan the specimen container 1 longitudinally at a rapid rate. With this arrangement, only a short length of the container 1 equal to the width of the flying spot of light is illuminated at any instant. The background noise is proportionately reduced. The light scatted by a platelet clump during the time that the spot of light illuminates the clump is unaffected, so that a train of pulses results which are sufficiently great in amplitude with respect to the background noise to give a reliable signal when the platelet clumps begin to stick to the wall of the specimen container 1.

Since the signal denoting the presence of platelet clumps now consists of a train of pulses whose repetition rate is determined by the number of slits 33 in the rotating shutter 32 and its speed of rotation, the repetition rate of the flying spot can be controlled. This means that the signal to noise ratio could be still further improved by the use of resonant circuits or other frequency-selective means which distinguish between a random pulse and a repetitive pulse train.

With the above arrangement, the onset of clotting produces an important change in the signal pattern. Before clotting takes place, the signal consists of a series of pulse trains which, if coming from a photodiode detector, are DC pulses. That is, they increase positively or negatively from a baseline level. The number of pulse trains increases and may overlap as the number of platelet clumps sticking to the container 1 increases, but between pulses, the signal basically returns to the baseline level. Detection can therefore be carried out by feeding the pulse train directly to a differential comparator which is offset by a predetermined threshold voltage. As soon as the pulse arrives that is greater than the offset threshold, the comparator will give an output pulse. The output pulse from the comparator is arranged to stop a timer which had been started when the blood specimen was introduced into the container. The time interval measured by the timer is the sticking time, indicating platelet activity. When clotting occurs, a fibrin net appears on the wall of the container 1 and rapidly covers the whole length of the container. This has the effect of dispersing light into the sensor array 30 wherever the scanning spot of light is positioned along the container 1. If a photodiode array is used for the sensor array 30, the DC output voltage of the photodiode array does not return to the baseline level. This, in effect, produces a DC offset signal which is characteristically quite different from the effect produced by the train of pulses from a platelet clump. The latter are very short duration pulses so that their average DC offset is very small. All that is necessary, therefore, to distinguish between sticking and clotting is to apply the photodiode output signal to a DC buffer amplifier and then split the output of this amplifier into two channels for detection of the two different types of signals.

Figure 4:
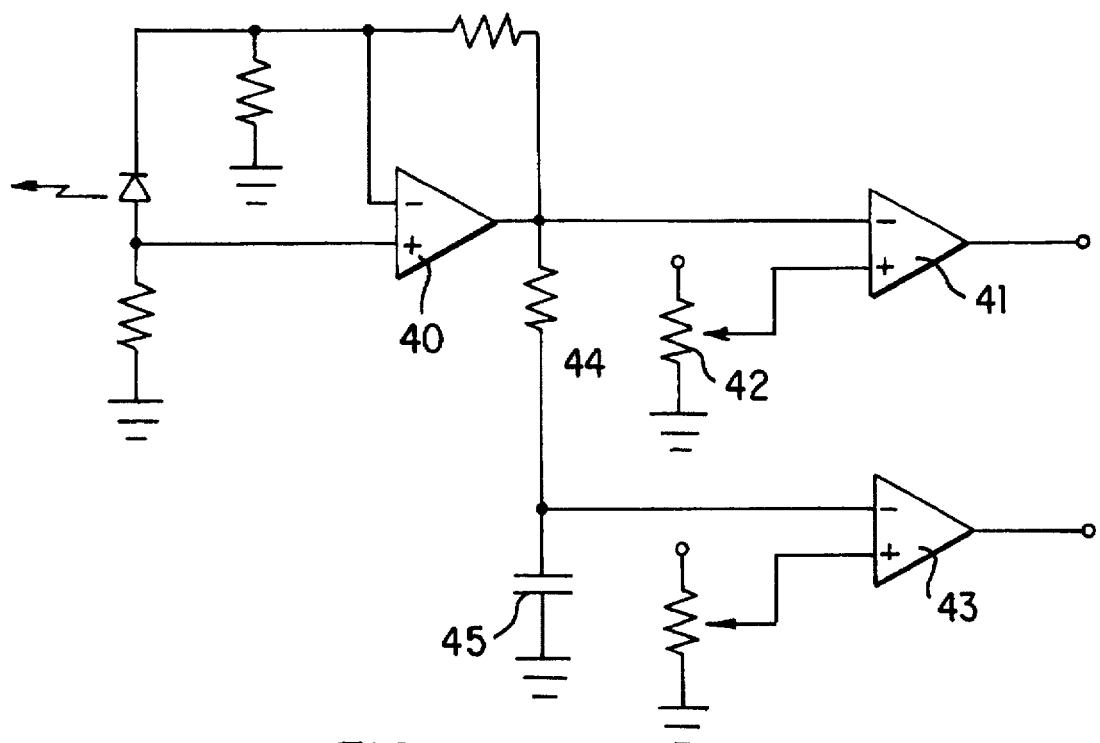
FIG. 4 is a schematic diagram of an amplifier and signal discrimination circuit for use in conjunction with the end-point detector shown in FIG. 3.

One such circuit for accomplishing this is shown in FIG. 4. In a preferred embodiment, the buffer amplifier is an operational amplifier 40. The output of the operational amplifier 40 is split. One portion goes directly to a first differential comparator 41 which has an offset threshold voltage applied to its other input through a potentiometer 42. The potentiometer 42 permits placing a suitable threshold value into the first comparator 41. The other portion of the output signal goes to a second differential comparator 43 via a simple low pass filter (resistor 44 and capacitor 45), which ensures that none of the relatively high-frequency pulses reaching the first comparator 41 also reach the second comparator 43. The second comparator 43 is thus sensitive only to the DC offset produced by the formation of the fibrin net, which signifies the onset of clotting. The outputs of first and second comparators 41, 43 are used to stop timers (not shown), respectively giving the sticking time and clotting time for the specimen.

As an alternative to the embodiment shown in FIG. 4, a steady line light source can be used, and the sensor array can be electronically scanned, thereby mimicking the effect of the flying spot apparatus described above.

Some disadvantages exist in having the photosensor inside the specimen container 1. One disadvantage is that the specimen container 1 must be end-loaded into the inventive apparatus. A second disadvantage is that the sensor array 30 is in very close proximity to the specimen fluid 2 in the container 1, and may become contaminated. It is therefore more desirable to situate a photosensor outside of the specimen container.

It has been found experimentally that the onset of sticking can be induced near the open end of a specimen container 1 by deliberately tilting the container downwards towards the open end. The strong surface tension of the contained fluid, aided by the radius of curvature of the rim of the specimen container 1 helps prevent spillage. When the specimen container 1 was tilted towards the open end, it was observed that sticking in fact first took place regularly near the open end. This phenomenon permits using a light source to scan the inside of the specimen container 1 through its open end such that light passes through only one wall of the specimen container 1. A photosensor is placed outside of the specimen container 1 to detect light passing through the specimen container 1. Thus, imperfections in the specimen container 1 and the dispersing light effect on the thin layer of red cells and disclosure reagent adhering to the inner wall of the specimen container 1 have a minimal effect on the sensing system.

FIG. 5 illustrates one apparatus that implements this arrangement. An intense collimated light source 50 (for example, a small solid-state laser) is mounted so that it rocks with the specimen container 1. The light source 50 emits a small-diameter (e.g., 1 mm) light beam directed against a vibrating mirror 51 (for example, in a mirror galvanometer) which causes the light beam to scan the inner surface of a specimen container through its open end. The scanning rate is not critical, and 60 Hz has been found to be sufficiently fast. The light beam is aimed at the horizontal midplane of the specimen container 1, so that it does not pass through the specimen fluid 2. As desired, the light beam passes through only one wall of the specimen container 1, which provides an improved signal-to-noise ratio.

A photosensor or photosensor array 52 is provided adjacent and external to the specimen container 1. If no platelet clumps are stuck to the inner surface of the specimen container 1 near its open end, the light beam passes by the photosensor 52, and thus generates no output in the photosensor 52. When a platelet clump sticks to the inner surface, the light beam is scattered and some falls on the photosensor 52. The arrangement is efficient because the scatter amounts to low-angle dispersion and the collecting area is large. The light beam is very intense, so that the output is large, thus ensuring that the instrument is relatively insensitive to stray electrical interference.

This arrangement has the advantages of the internal photosensor instrument described above, without the disadvantages. The same discrimination between sticking time and clotting time can be obtained because of the short pulses produced by the platelet clumps as they are scanned by the light beam, and the DC offset signal produced by the fibrin net laid down on the interior wall of the specimen container 1 as the specimen fluid 2 begins to clot.

FIG. 6 shows yet another apparatus incorporating the concepts of the present invention, but for detecting the clumping time endpoint. In the device shown in FIG. 6, collimated light from a light source 60 is made to shine through a slit diaphragm 61 through the top of a specimen container 1. The light beam passes downwards through the specimen fluid 2 and the lower wall of the specimen container 1 into a photosensor 62, such as a photodiode. The specimen container 1 both rotates and rocks so that the specimen fluid 2 is moving in a wave-like motion back and forth in the container 1. Until platelet clumps form, however, there are essentially no visible particles in the container 1 since red cells and disclosure reagent particles are very small. As soon as platelet clumps form, they incorporate disclosure reagent particles and form clearly visible clumps which appear dark in color. These clumps are still free to move within the specimen fluid 2 and so drift back and forth past the light beam. A very complex signal emerges from the photosensor 62. Variations in the photosensor 62 signal are due to a number of factors: the presence of platelet/disclosure reagent particle clumps; the varying depth of specimen fluid 2 in the light path as the apparatus rocks and rotates; imperfections in the specimen container 1; and some dispersion of the light due to red blood cells and disclosure reagent being carried around the interior wall of the specimen container 1.

However, it has been found that most of the different parts of this complex signal can be separated because they have different frequency characteristics. The signal generated from the effects associated with the rotation and rocking of the specimen container 1 have a very low frequency. The signal generated by very small particles clinging to the interior of the specimen container 1 have a high frequency. The signal generated by platelet clumps has an intermediate frequency. If high-quality specimen containers are used, optical imperfections of the specimen containers have a reduced effect on the intermediate frequencies of the output signals. Therefore, with appropriate signal processing, this method can be used to detect the clumping time of the specimen fluid 2.

Figure 7:
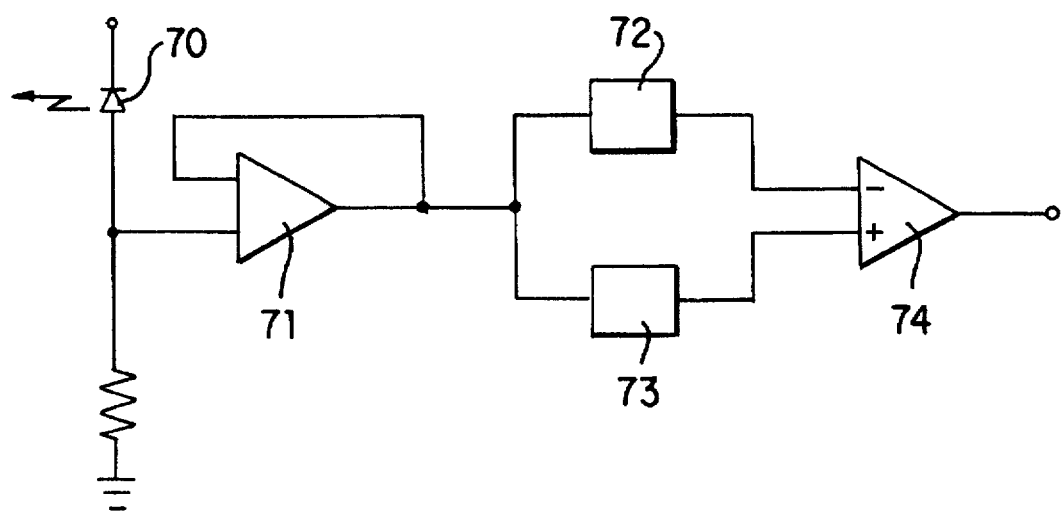
FIG. 7 is a schematic diagram of an amplifier and signal discrimination circuit for use in conjunction with the end-point detector shown in FIG. 6.

An appropriate signal processing circuit is shown in FIG. 7. The photosensor comprises a photodiode sensor 70, which is coupled to a buffer amplifier 71. The output of the buffer amplifier 71 is split into two channels, which feed two time-delay circuits 72, 73, or suitable band pass filters. The output of the time-delay circuits are fed to the inputs of a differential amplifier 74, from which the final signal is taken. If the period of the variant signal from the photodiode sensor 70 is sufficiently low so that the two time delay circuits 72, 73 give substantially equal outputs, the differential amplifier 74 will receive equal signals at its inverting and noninverting inputs. Due to the common mode rejection capability of the differential amplifier 74, no signal will appear at the output. If, however, a sudden signal spike is generated by the photodiode sensor 70 due to the small size and rapid transit of a platelet clump and one time delay circuit 72 has a slightly shorter time delay than the other time delay circuit 73, a signal will appear at the output of the first time delay circuit 72 before a signal appears at the output of the second time delay circuit 73. This unbalances the inputs to the differential amplifier 74, and results in a signal at the output. This will be followed by an output of opposite polarity as the signal from the second time delay circuit 73 reaches the input of the differential amplifier 74, and the signal from the first time delay circuit 72 terminates. A 30 millisecond differential between the two time delay circuits 72, 73 has been found to provide good clump detection. The frequency and amplitude of the signal from 74 discloses both the rate of growth and the size of the platelet clumps.

Thus, combining the detection apparatus shown in FIG. 6 with the apparatus shown in either FIG. 3 or FIG. 5, results in a fully-automated instrument that detects the clumping time, sticking time, and clotting time for a specimen fluid.

EXAMPLE 1

The clumping, sticking, and clotting times under various test conditions was determined for normal as well as certain abnormal patient specimens. Typical values which were obtained are shown in Table 1. The values listed in this table would normally be redetermined for each laboratory and with each new lot of reagents. As shown in Table 1, values are given for the various patient conditions as determined by reagent tests which utilize dry celite alone, or dry celite in combination with ristocetin, ADP, arachidonic acid, and collagen.

Each of these tests is performed as described above. In brief, the blood is mixed with the celite and placed in the device to allow rocking and tilting until the various sticking, clumping, and clotting steps are noted. When one of the additional platelet agonists is used, it is added to the dry celite mixture at the beginning of the test. Typically, a patient sample would be tested using all five test protocols in evaluating a given sample to determine the status of the patient.

Although the present invention has been described in connection with a particular embodiment thereof, additional embodiments, applications and modifications, which will be obvious to those skilled in the art, are included within the spirit and scope of the invention. For example, the inventive apparatus can be adapted to rotate and rock more than one specimen container at a time. Different light sources can be used, including light-emitting diodes, halogen light sources, and the like. The light used can be visible or non-visible wavelengths (e.g., infrared). Alternative amplification and discrimination circuits can be used. Different motions can be imparted to a specimen container, so long as the specimen fluid is caused to coat a substantial portion of the wall of the container. Therefore, this invention is not to be limited to the specific embodiment discussed and illustrated herein, but rather by the following claims.

TABLE 1

TEST PHASE PARAMETERS FOR VARIOUS SPECIMENS USING DIFFERENT REAGENT TESTS[a]

| Patient Condition | Test Phase | Dry Celite Alone | Dry Celite + Ristocetin | Dry Celite + ADP | Dry Celite + Arach Acid | Dry Celite + Collagen |
|---|---|---|---|---|---|---|
| Normal | Clumping | 27–33 | 36–56 | 20–30 | 27–47 | 46–82 |
|  | Sticking | 36–46 | 50–76 | 30–42 | 39–59 | 77–97 |
|  | Clotting | 96–116 | 168–238 | 119–149 | 137–163 | 160–180 |
| Potentially aspirin curable hyper-coagulability | Clumping | 30–33 | 36–56 | 20–30 | <25 | 74–82 |
|  | Sticking | 41–46 | 50–76 | 30–42 | <37 | 90–97 |
|  | Clotting | 96–116 | 168–238 | 119–149 | 137–163 | 160–180 |
| Platelet Factor 3 Release Defect (assuming normal PT and PTT) | Clumping | 27–33 | 36–56 | 20–30 | 27–47 | 46–82 |
|  | Sticking | 36–46 | 50–76 | 30–42 | 39–59 | 77–97 |
|  | Clotting | >125 | >250 | >160 | >175 | >190 |
| Disseminated Intravascular Coagulation | Clumping | >40 | >60 | >35 | >55 | >90 |
|  | Sticking | >50 | >80 | >45 | >65 | >100 |
|  | Clotting | >120 | >250 | >170 | >180 | >190 |
| Storage Pool Lesion of Myeloproliferative Disease (or possible drug effect) | Clumping | >45 | 36–56 | >45 | >55 | >90 |
|  | Sticking | >55 | 50–76 | >55 | >70 | >100 |
|  | Clotting | >125 | 168–238 | >160 | >180 | >190 |
| Aspirin or other cyclooxygenase inhibitor effect | Clumping | >40 | 36–56 | 20–30 | 27–47 | >90 |
|  | Sticking | >50 | 50–76 | 30–42 | 39–59 | >100 |
|  | Clotting | >120 | 168–238 | 119–149 | 137–163 | >190 |
| Defect in Clotting Phase | Clumping | 27–33 | 36–56 | 20–30 | 27–47 | >46–82 |
|  | Sticking | 36–46 | 50–76 | 30–42 | 39–59 | >77–97 |
|  | Clotting | >120 | >250 | >160 | >180 | >190 |
| Partially Recovered Drug Effect | Clumping | >40 | 36–56 | 20–30 | >55 | >90 |
|  | Sticking | >50 | 50–76 | 30–42 | >70 | >100 |
|  | Clotting | >120 | 168–238 | 119–149 | >180 | >190 |
| Glanzmann's Thrombasthenia | Clumping | >100 | >60 | >100 | >100 | >125 |
|  | Sticking | >100 | >80 | >100 | >100 | >150 |
|  | Clotting | >125 | >250 | >160 | >180 | >200 |
| Bernard Soulier Syndrome | Clumping | 27–33 | >100 | 20–30 | 27–47 | 46–82 |
|  | Sticking | 36–46 | >150 | 30–42 | 39–59 | 77–97 |
|  | Clotting | 96–116 | >250 | >119–149 | 137–163 | 160–180 |
| Grey Platelet Syndrome | Clumping | >40 | 36–56 | >35 | 27–47 | >90 |
|  | Sticking | >50 | 50–76 | >45 | 39–59 | >100 |
|  | Clotting | >120 | 168–238 | >170 | 137–163 | >190 |
| Hermansky-Pudlak Syndrome | Clumping | >40 | >60 | >45 | 27–47 | >90 |
|  | Sticking | >50 | >80 | >55 | 39–59 | >100 |
|  | Clotting | >120 | >250 | >160 | 137–163 | >190 |
| Heparin Anticoagulation Monitoring (Patient Adequately Anticoagulated) | Clumping | 27–33 | 36–56 | 20–30 | 27–47 | 46–82 |
|  | Sticking | 36–46 | 50–76 | 30–42 | 39–59 | 77–97 |
|  | Clotting | >120 | >250 | >160 | >180 | >190 |
| Coumadin Anticoagulation Monitoring (Patient Adequately Anticoagulated) | Clumping | 27–33 | 36–56 | 20–30 | 27–47 | 46–82 |
|  | Sticking | 36–46 | 50–76 | 30–42 | 39–59 | 77–97 |
|  | Clotting | >120 | >250 | >160 | >180 | >190 |
| Aspirin or other cyclooxygenase inhibitor effect | Clumping | >40 | 36–56 | 20–30 | 27–47 | >90 |
|  | Sticking | >50 | 50–76 | 30–42 | 39–59 | >100 |
|  | Clotting | >120 | 168–238 | 119–149 | 137–163 | >190 |
| Defect in Clotting Phase | Clumping | 27–33 | 36–56 | 20–30 | 27–47 | >46–82 |
|  | Sticking | 36–46 | 50–76 | 30–42 | 39–59 | >77–97 |
|  | Clotting | >120 | >250 | >160 | >180 | >190 |
| Partially Recovered Drug Effect | Clumping | >40 | 36–56 | 20–30 | >55 | >90 |
|  | Sticking | >50 | 50–76 | 30–42 | >70 | >100 |
|  | Clotting | >120 | 168–238 | 119–149 | >180 | >190 |
| Glanzmann's Thrombasthenia | Clumping | >100 | >60 | >100 | >100 | >125 |
|  | Sticking | >100 | >80 | >100 | >100 | >150 |
|  | Clotting | >125 | >250 | >160 | >180 | >200 |
| Bernard Soulier Syndrome | Clumping | 27–33 | >100 | 20–30 | 27–47 | 46–82 |
|  | Sticking | 36–46 | >150 | 30–42 | 39–59 | 77–97 |
|  | Clotting | 96–116 | >250 | >119–149 | 137–163 | 160–180 |
| Grey Platelet Syndrome | Clumping | >40 | 36–56 | >35 | 27–47 | >90 |
|  | Sticking | >50 | 50–76 | >45 | 39–59 | >100 |
|  | Clotting | >120 | 168–238 | >170 | 137–163 | >190 |
| Hermansky-Pudlak Syndrome | Clumping | >40 | >60 | >45 | 27–47 | >90 |
|  | Sticking | >50 | >80 | >55 | 39–59 | >100 |
|  | Clotting | >120 | >250 | >160 | 137–163 | >190 |
| Heparin Anticoagulation Monitoring (Patient Adequately Anticoagulated) | Clumping | 27–33 | 36–56 | 20–30 | 27–47 | 46–82 |
|  | Sticking | 36–46 | 50–76 | 30–42 | 39–59 | 77–97 |
|  | Clotting | >120 | >250 | >160 | >180 | >190 |

TABLE 1-continued

TEST PHASE PARAMETERS
FOR VARIOUS SPECIMENS USING DIFFERENT REAGENT TESTS*

| Patient Condition | Test Phase | Dry Celite Alone | Dry Celite + Ristocetin | Dry Celite + ADP | Dry Celite + Arach Acid | Dry Celite + Collagen |
|---|---|---|---|---|---|---|
| Coumadin Anti-coagulation Monitoring (Patient Adequately Anticoagulated) | Clumping | 27–33 | 36–56 | 20–30 | 27–47 | 46–82 |
| | Sticking | 36–46 | 50–76 | 30–42 | 39–59 | 77–97 |
| | Clotting | >120 | >250 | >160 | >180 | >190 |

*time in seconds

We claim:

1. A method for detecting platelet aggregation in an apparatus for optically measuring characteristics of a platelet-containing specimen fluid, comprising the steps of:
   (a) forming a mixture consisting of a disclosure reagent which adheres to platelets with a diluent and at least one platelet agonist which activates platelets and initiates platelet clumping;
   (b) lyophilizing the mixture; and,
   (c) placing the mixture and specimen fluid into the apparatus and detecting platelet aggregation by visualizing and measuring the platelet clumping without contacting the specimen fluid with a foreign measuring object.

2. The method of claim 1, wherein the diluent is a saline solution.

3. The method of claim 1, wherein the specimen fluid is whole blood.

4. The method of claim 3, wherein the whole blood is anticoagulated before being placed into the apparatus with the mixture.

5. The method of claim 1, further including a step of adding a soluble calcium salt to the mixture before the step of lyophilizing the mixture.

6. The method of claim 1, wherein the disclosure reagent is diatomaceous earth.

7. The method of claim 1, wherein the platelet agonist is a catecholamine.

8. The method of claim 1, wherein the platelet agonist further comprises humic acid.

9. The method of claim 1 wherein the mixture includes a first platelet agonist selected from the group consisting of humic acid, arachidonic acid, adenosine diphosphate, ristocetin and collagen.

10. The method of claim 9 wherein the mixture includes a second platelet agonist, wherein the second platelet agonist is a catecholamine.

11. The method of claim 10, wherein the catecholamine is selected from the group consisting of epinephrine, noradrenaline, or dopamine.

12. The method of claim 13 wherein the disclosure reagent is nylon fiber, finely chopped glass or finely chopped fiberglass.

* * * * *